US011622924B2

(12) United States Patent
Haskel et al.

(10) Patent No.: US 11,622,924 B2
(45) Date of Patent: Apr. 11, 2023

(54) SYSTEM AND METHOD FOR MAKING AN ORAL CARE FORMULATION

(71) Applicants: Colgate-Palmolive Company, New York, NY (US); NIZO FOOD RESEARCH B.V., Ede (NL)

(72) Inventors: Ariel Haskel, East Brunswick, NJ (US); Jessica Monk, Voorhees, NJ (US); Najma Khan, Somerset, NJ (US); Kerstin Burseg, Ede (NL); Peter De Kok, Ede (NL); Ann Stijnman, Ede (NL)

(73) Assignee: Colgate-Palmolive Company, New York, NY (US)

( * ) Notice: Subject to any disclaimer, the term of this patent is extended or adjusted under 35 U.S.C. 154(b) by 256 days.

(21) Appl. No.: 14/905,770

(22) PCT Filed: Jul. 16, 2014

(86) PCT No.: PCT/US2014/046925
§ 371 (c)(1),
(2) Date: Jan. 15, 2016

(87) PCT Pub. No.: WO2015/009876
PCT Pub. Date: Jan. 22, 2015

(65) Prior Publication Data
US 2016/0151252 A1 Jun. 2, 2016

Related U.S. Application Data

(60) Provisional application No. 61/846,961, filed on Jul. 16, 2013.

(51) Int. Cl.
*A61C 17/02* (2006.01)
*A61K 8/18* (2006.01)
(Continued)

(52) U.S. Cl.
CPC .............. *A61K 8/18* (2013.01); *A46B 11/063* (2013.01); *A61C 17/0217* (2013.01);
(Continued)

(58) Field of Classification Search
CPC ................ A61K 8/18; A61K 2800/591; A61K 2800/805; A61K 2800/884;
(Continued)

(56) References Cited

U.S. PATENT DOCUMENTS 4,348,378 A    9/1982  Kosti et al.
4,820,506 A *  4/1989  Kleinberg .............. A61K 33/42
                                                    424/40
(Continued)

FOREIGN PATENT DOCUMENTS

GB       1054431           1/1967
GB       WO 0241801 A1 *   5/2002  ............... A61K 8/02
(Continued)

OTHER PUBLICATIONS

International Search Report and Written Opinion of International Application No. PCT/US/2014/046925, dated Oct. 13, 2014.

*Primary Examiner* — Ralph A Lewis

(57) ABSTRACT

Systems and methods for mixing an oral care formulation base with one or more oral care additives in-situ. In one aspect, the invention can be a method of making an oral care formulation for consumer use, the method comprising: a) providing a first dose of an oral care formulation base to an oral cavity of a test subject; b) dispensing one or more oral care additives to the oral cavity in accordance with a first dispensing regimen during the performance of step a), the one or more oral care additives mixing with the first dose of the oral care formulation base in-situ within the oral cavity of the test subject; c) obtaining feedback regarding effects experienced by the test subject during the performance of (Continued)

step b); and d) creating the oral care formulation for consumer use based, at least in part, on the feedback of step c).

13 Claims, 7 Drawing Sheets

(51) Int. Cl.
*A61Q 11/00* (2006.01)
*A46B 11/06* (2006.01)
*A61C 17/22* (2006.01)

(52) U.S. Cl.
CPC ...... *A61Q 11/00* (2013.01); *A46B 2200/1066* (2013.01); *A61C 17/227* (2013.01); *A61K 2800/591* (2013.01); *A61K 2800/805* (2013.01); *A61K 2800/884* (2013.01); *A61K 2800/92* (2013.01); *A61K 2800/95* (2013.01)

(58) Field of Classification Search
CPC ............ A61K 2800/92; A61K 2800/95; A46B 11/063; A46B 2200/1066; A61C 17/0217; A61C 17/227; A61Q 11/00
USPC ........................................................ 433/215
See application file for complete search history.

(56) References Cited

U.S. PATENT DOCUMENTS

| 6,241,974 | B1 | 6/2001 | White et al. |
| 6,596,298 | B2* | 7/2003 | Leung ................ A23G 3/50 424/405 |
| 6,648,641 | B1* | 11/2003 | Viltro ................ A61K 8/02 132/308 |
| 2007/0254067 | A1 | 11/2007 | Ha et al. |
| 2009/0098505 | A1 | 4/2009 | Randolph et al. |
| 2011/0081628 | A1* | 4/2011 | Alden, IV .......... A46B 15/0055 433/216 |
| 2012/0082630 | A1* | 4/2012 | Haught .................. A61K 8/602 424/54 |

FOREIGN PATENT DOCUMENTS

| WO | WO 2002/41801 | 5/2002 |
| WO | WO 2008/147360 | 12/2008 |
| WO | WO 2012/106016 | 8/2012 |
| WO | WO 2013/001520 | 1/2013 |

* cited by examiner

SYSTEM AND METHOD FOR MAKING AN ORAL CARE FORMULATION

CROSS REFERENCE TO RELATED APPLICATIONS

This application is a United States Application under 35 U.S.C. 371 claiming benefit of PCT Application No. PCT/US2014/046925, filed on Jul. 16, 2014, which claims the benefit of U.S. Provisional Application No. 61/846,961, Jul. 16, 2013, the contents of each of which are incorporated herein by reference in their entireties.

BACKGROUND OF THE INVENTION

In order to test an oral care formulation, a prototype of the oral care formulation must be created so that a test subject can try or test out the oral care formulation. The experimental testing of oral care formulations containing materials that impart a sensation is a time consuming process which requires the making of many prototypes. These oral care formulations are made with an oral care formulation base, a combination of oral care additives and varying material levels of the oral care additives. The need to create many prototypes with varying oral care additives and material levels can be an expensive process. Specifically, the number of prototypes that need to be created in order to test out all of the different variations of the oral care additives is incredibly high, leading to high costs during the testing stages. Additionally, the assessment of prototypes that deliver the oral care additives in a time dependent fashion is generally unattainable. Thus, a need exists for a more efficient and effective method and system for making an oral care formulation that can be tested by a test subject without the need to create a full prototype formulation. A need also exists for a system and method for making an oral care formulation in-situ so that time-dependent feedback can be received from a test subject.

BRIEF SUMMARY OF THE INVENTION

The present invention is directed to a system and method of making an oral care formulation in-situ in a testing environment. Specifically, the present invention describes a method for delivering stimulus/stimuli, by way of oral care additives, into a test subject's mouth while an oral care formulation base is being used. The assessment of the material's effect can be done during exposure and thereafter. By using the inventive method, the delivery of the oral care additives can be varied in: (1) concentration level; (2) length of exposure; (3) number of materials; (4) time-dependency; (5) sequence of oral care additive dispensing; and other factors/parameters. Thus, the present invention may facilitate the assessment of all parameters (e.g. level of freshness, cleaning, cooling, warming, tingling, etc.) without the need to make a full batch of each prototype.

In one aspect, the invention can be a method of making an oral care formulation for consumer use, the method comprising: a) providing a first dose of an oral care formulation base to an oral cavity for a test subject; b) dispensing one or more oral care additives to the oral cavity in accordance with a first dispensing regimen during the performance of step a), the one or more oral care additives mixing with the first dose of the oral care formulation base in-situ within the oral cavity of the test subject; c) obtaining feedback regarding effects experienced by the test subject during the performance of step b); and d) creating the oral care formulation for consumer use based, at least in part, on the feedback of step c).

In another aspect, the invention can be a method of making an oral care formulation, the method comprising: a) providing an oral care formulation base to an oral cavity; and b) dispensing one or more oral care additives to the oral cavity in accordance with a dispensing regimen during the performance of step a), the one or more oral care additives mixing with the oral care formulation base in-situ within the oral cavity to create the oral care formulation.

In a further aspect, the invention can be a method of making oral care formulations, the method comprising: a) providing an oral care implement and a dispensing system comprising one or more reservoirs of oral care additives, one or more conduits fluidly coupling the one or more reservoirs to one or more outlets of the oral care implement, a programmable controller, and one or more flow control mechanisms operably coupled to the one or more reservoirs, the programmable controller operably coupled to the one or more flow control mechanisms; b) loading the oral care implement with an oral care formulation base; c) treating oral surfaces of an oral cavity with the oral care implement loaded with the oral care formulation base; and d) during step c), the programmable controller executing a selected dispensing regimen to dispense one or more oral care additives, in accordance with dispensing parameters of the selected dispensing regimen, from the one or more reservoirs into the oral cavity via the oral care implement, the one or more dispensed oral care additives mixing with the oral care formulation base in-situ within the oral cavity to form an oral care formulation.

In a still further aspect, the invention can be a system for making an oral care formulation, the system comprising: an oral care implement comprising one or more outlets; and a dispensing system comprising: one or more reservoirs of oral care additives; one or more conduits fluidly coupling the one or more reservoirs to the one or more outlets of the oral care implement; a programmable controller, and one or more flow control mechanisms operably coupled to the one or more reservoirs, the programmable controller operably coupled to the one or more flow control mechanisms to actuate the one or more flow control mechanisms in a manner such that the one or more oral care additives are dispensed via the outlets of the oral care implement in accordance with dispensing parameters of a selected dispensing regimen.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
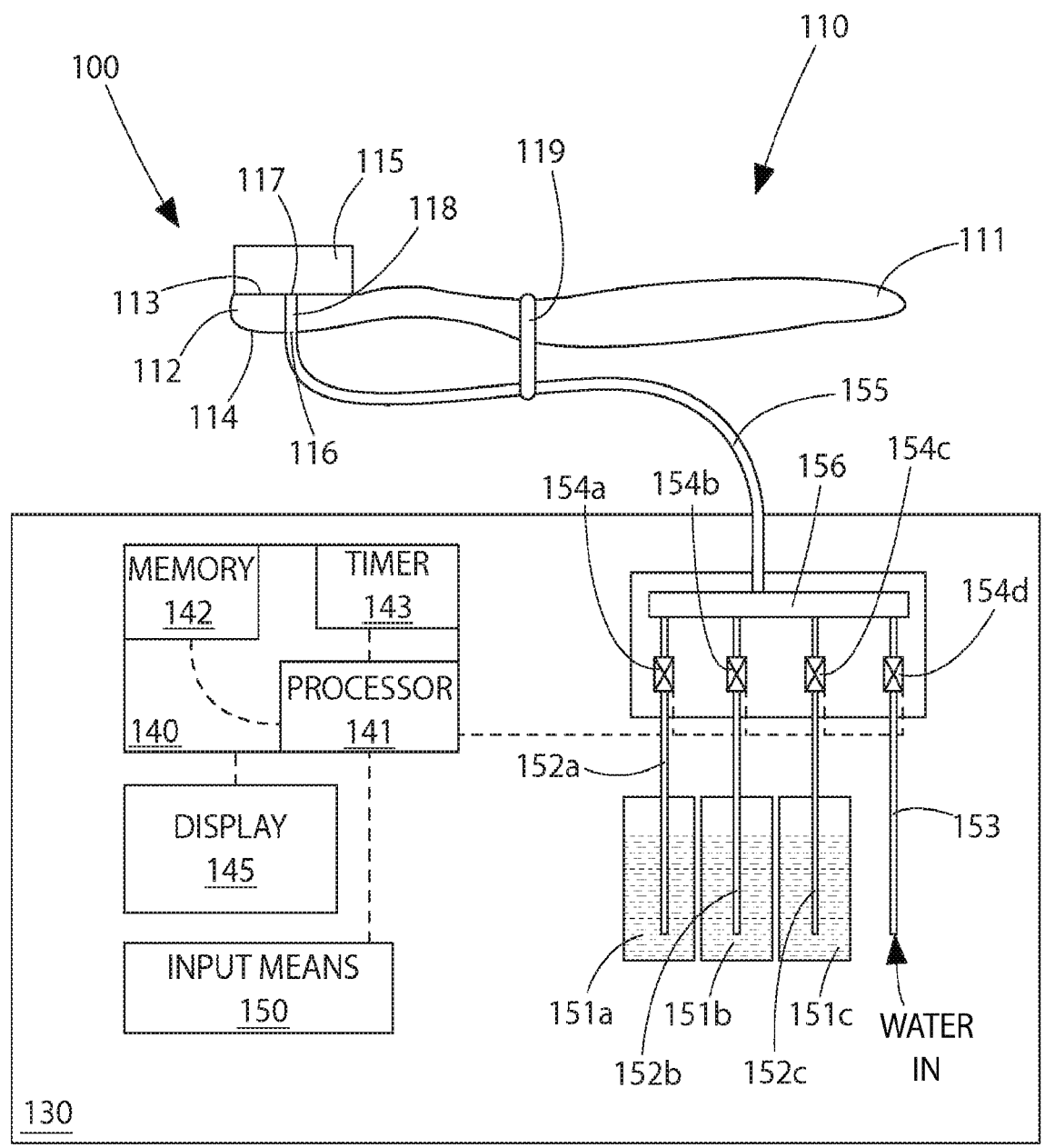
FIG. 1 is a schematic illustration of a system for making an oral care formulation in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

The present invention is directed to a system for making an oral care formulation as well as a method for making an oral care formulation. More specifically, utilizing the system and method disclosed herein, an oral care formulation that comprises an oral care formulation base as well as any of a variety of different oral care additives can be created in-situ within the oral cavity of a test subject. The oral care formulation base can be any type of oral care formulation to which oral care additives are then added to change the effect perceived by a user of the oral care formulation. In some embodiments, the oral care formulation base can be a flavorless oral care formulation or toothpaste. In other embodiments, the oral care formulation base can be a flavored oral care formulation or toothpaste, and the oral care additives can add new flavors or other materials that provide a user with various effects, increase concentration of the flavor, or otherwise modify the effect of the oral care formulation on the user. In still other embodiments, the oral care formulation base can be a rinse formula and oral care additives can be added directly into the test subject's oral cavity utilizing the inventive system to modify the flavor, sensory effects or the like. Thus, the oral care formulation base can be any type of base material to which oral care additives are added using the inventive system to change the flavor, sensory effects, trigeminal response or the like that is felt by a test subject so that the test subject can provide feedback regarding various dispensing regimens. Furthermore, in some embodiments the system and method disclosed herein can be used to obtain feedback regarding various oral care additives without the use of an oral care formulation base. Thus, in some embodiments the oral care formulation base may be altogether omitted and the oral care additives can be added directly to a test subject's oral cavity utilizing the inventive system 100 as will be discussed in more detail below.

In accordance with one embodiment of the inventive method, the test subject will begin by brushing his or her teeth with only the oral care formulation base or by rinsing his or her mouth when the oral care formulation base is a rinse formula. During brushing or rinsing, at various time increments/intervals as determined by pre-set algorithms and dispensing regimens, various oral care additives such as flavor additives, sensation additives, additives that cause a trigeminal response or the like can be dispensed or injected into the test subject's oral cavity. The additives that are dispensed into the test subject's oral cavity will mix with the non-flavored oral care formulation base to create a prototype of an oral care formulation in-situ in the test subject's oral cavity. The test subject can then provide feedback regarding his or her experience with the particular oral care formulation created in-situ. Thus, using an oral care formulation base and injecting various oral care additives according to different recipes or dispensing regimens into the user's oral cavity, the user can experience the effects of an oral care formulation that could be created using the oral care formulation base and the additives.

Referring first to FIG. 1, a system 100 for making an oral care formulation is illustrated in accordance with a first embodiment of the present invention. The system 100 generally comprises an oral care implement 110 and a dispensing system 130. In the exemplified embodiment, the oral care implement 110 is illustrated as a toothbrush. However, the invention is not to be so limited and in other embodiments the oral care implement can take the form of a soft-tissue cleansing implement, an inter-proximal pick, a flossing tool, a plaque scraper, a powered toothbrush, or other ansate implement designed for oral care. It is also to be understood that other embodiments may be utilized, and that structural and functional modifications may be made without departing from the scope of the present invention. Furthermore, as will be discussed in detail below, in certain embodiments the oral care implement 110 may be omitted and the oral care additives can be dispensed directly into a test subject's oral cavity from the dispensing system 130 without using the oral care implement 110 as an intermediary application device. For example, when the oral care formulation base is a rinse formula, it may not be desirable to have a test subject brushing his or her teeth using the oral care implement 110, but rather it may be preferable to directly dispense or inject the oral care additives into the test subject's oral cavity.

As noted above, in the exemplified embodiment the oral care implement 110 is a toothbrush. The oral care implement 110 comprises a handle 111 and a head 112. In one embodiment, the head 112 and the handle 111 can be formed as an integral structure using an injection molding process. In other embodiments, however, the handle 111 and the head 112 may be formed as separate components which are coupled together at a later stage of the manufacturing process by any suitable technique known in the art, including without limitation thermal welding, sonic welding, a tight-fit assembly, a coupling sleeve, adhesion, or fasteners. Whether the head 112 and the handle 111 are constructed as a single integral component or a multi-piece assembly (including connection techniques) is not limiting of the present invention in all embodiments, unless specifically recited in the claims. Furthermore, other manufacturing techniques may be used in place of and/or in addition to injection molding to create the handle 111 and/or the head 112, such as milling and/or machining. The specific dimensions, shape, structure and the like of the oral care implement 110 are not to be limiting of the present invention in all embodiments, and in certain embodiments the oral care implement can be any structural feature that is capable of being fluidly coupled to the dispensing system 130 as discussed below in order to dispense an oral care formulation to a consumer or test subject.

The head 112 of the oral care implement 110 comprises a front surface 113 and an opposite rear surface 114. A plurality of tooth cleaning elements 115 extend outwardly from the front surface 113 of the head 112 for cleaning contact with a user's teeth. Common examples of "tooth cleaning elements" include, without limitation, filament bristles, fiber bristles, nylon bristles, spiral bristles, rubber bristles, elastomeric protrusions, flexible polymer protrusions, co-extruded filaments, flag bristles, crimped bristles, anti-bacterial bristles and combinations thereof and/or structures containing such materials or combinations. In one embodiment, the tooth cleaning elements 115 comprises bristle tufts. In another embodiment, the tooth cleaning elements 115 comprises both bristle tufts and elastomeric elements. The tooth cleaning elements 115 can be secured to the head 112 of the oral care implement 110 in any manner known in the art, including without limitation in-mold tufting (IMT), stapling techniques, or anchor free tufting (AFT). Furthermore, various soft tissue cleaners formed of elastomeric materials (i.e., thermoplastic elastomers) or the like and having nubs, ridges or the like can be coupled to the rear surface 114 of the head 112 for providing a cleaning or scrubbing action to a user's soft tissue surfaces and tongue.

In the exemplified embodiment, the head 112 of the oral care implement 110 comprises a port 116 and an outlet 117 that is in fluid communication with the port 116. The port 116 forms an opening in the rear surface 114 of the head 112 and the outlet 117 forms an opening in the front surface 113 of the head 112. A passageway 118 extends through the head 112 from the port 116 to the outlet 117 so that fluid can be supplied to the port 116 from the dispensing system 130, can flow through the passageway 118, and can then be dispensed from the outlet 117 into the oral cavity of a test subject. Thus, the combination of the port 116, the passageway 118 and the outlet 117 forms a through-hole through the head 112 of the oral care implement 110 that extends from the front surface 113 of the oral care implement 110 to the rear surface 114 of the oral care implement 110.

In the exemplified embodiment, the oral care implement 110 comprises a single port 116, passageway 118 and outlet 117. However, the invention is not to be so limited and in certain other embodiments the oral care implement 110 can comprise multiple ports, passageways and/or outlets. Specifically, in certain embodiments (such as the embodiment exemplified in FIG. 1) one or more oral care additives can be mixed together prior to being supplied to the oral care implement 110, in which case a single port 116 is capable of receiving the additives. However, in other embodiments the oral care additives may not be mixed until within a test subject's oral cavity, in which case multiple ports, outlets and passageways may be desired. In still other embodiments, the oral care implement 110 may comprise multiple ports, and the passageways formed into the head 112 extending from the ports may converge into a single outlet so that the oral care additives that are introduced into the ports are mixed within the oral care implement 110. Such embodiments will be discussed in more detail below with reference to FIGS. 2 and 3.

Still referring to FIG. 1, the dispensing system 130 comprises all of the components for executing a dispensing regimen and dispensing one or more oral care additives through the oral care implement 110 and to a test subject's oral cavity. Specifically, the dispensing system 130 generally comprises a programmable controller 140, a display 145, an input means 150, a plurality of reservoirs 151a, 151b, 151c, a plurality of conduits 152a, 152b, 152c, a water conduit 153 and a plurality of flow control mechanisms 154a, 154b, 154c, 154d. The programmable controller 140 comprises at least a processor 141, a memory 142 and a timer 143. In the exemplified embodiment, the dispensing system 130 is completely external to the oral care implement 110 and is fluidly coupled to the oral care implement 110 (specifically to the port 116 of the oral care implement 110) via one or more conduits, tubes or the like as discussed in more detail below. However, in certain other embodiments the dispensing system 130 may be housed in the handle 111 of the oral care implement 110 for dispensing oral care additives to and through the head 112 of the oral care implement. In such embodiments, various passageways can be formed within the handle 111 and the head 112 of the oral care implement 110 for flowing the oral care additives from the dispensing system 130 through the oral care implement 110 for dispensing to a test subject's oral cavity via the outlet 117.

In the exemplified embodiment the dispensing system 130 comprises three reservoirs 151a, 151b, 151c. The invention is not to be so limited and more or less than three reservoirs can be used in other embodiments. Each of the reservoirs 151a-c contains an oral care additive therein. In certain embodiments, each of the reservoirs 151a-c contains a different oral care additive therein. The oral care additives are any type of material that can be used as stimuli in an oral care formulation. Non-limiting examples of materials that can be used as the oral care additives in the reservoirs 151a-c include sweet doublemint dentifrice flavor, FC brighter flavor, optaheat fire, lemon oil, grape seed extract, coconut oil, water and the like. A non-exhaustive list of possible ingredients that can be used as the oral care additives is provided in Table 1 below along with maximum concentration of the oral care additive for use in an oral care formulation. It should be appreciated that the concentrations listed in Table 1 are maximum concentrations and various ranges of the concentrations below and/or including the maximum concentrations may be used (e.g., from 0.1% to the maximum concentration value for that particular oral care additive, from 0.01% to the maximum concentration value for that particular oral care additive, from 0.001% to the maximum concentration value for that particular oral care additive, or the like). In certain other embodiments, the oral care additives can be dispensed at concentrations that exceed that which is noted in Table 1. Furthermore, it should be appreciated that ingredients other than those noted in Table 1 can be used with the present invention.

TABLE 1

| Ingredient | Maximum Concentration (relative to 1.5 g flavorless toothpaste base) |
|---|---|
| Sweet Doublemint Dentifrice Flavor K91 | 0.9% |
| Basic Formulation + FC Brighter Flavor K91-5661 | 2.0% |
| Optaheat Fire | 1.55% |
| Lemon Oil | 0.3% |
| Grape Seed Extract | 0.3% |
| Coconut Oil | 2.5% |
| FC Brighter Flavor K91-5661 | 2.0% |

In certain embodiments, one or more of the oral care additives may comprise a functional material. As referred to herein, a "functional material" is a material having a desired utility in an oral care formulation. In some embodiments such utilities are therapeutic, cosmetic, aesthetic, decorative, sensory or combinations thereof.

In various embodiments, the functional material is a flavorant. In some embodiments, a flavorant is rapidly released and delivers a breath freshening flavor or desired mouth feel or sweetness into the oral cavity. Flavorants among those useful herein include synthetic flavor oils or flavoring aromatics, oleo resins and extracts derived from plants, leaves, flowers, fruits and so forth, and combinations thereof. Representative flavor oils include spearmint oil, cinnamon oil, peppermint oil, clove oil, bay oil, thyme oil, cedar leaf oil, oil of nutmeg, oil of sage, and oil of bitter almonds. Flavorants can be used individually or in admixture. Commonly used flavors include mints such as peppermint, artificial vanilla, cinnamon derivatives, and various fruit flavors. In certain embodiments, the film comprises flavoring or food additive, such as those described in Chemicals Used in Food Processing, publication 1274 by the National Academy of Sciences, pages 63-258. In various embodiments, the oral care additive may comprise a flavorant at a level of from about 1% to about 30% by weight of the oral care additive, or from about 8% to about 25% by weight of the oral care additive.

In some embodiments, the functional material is a sweetener. Sweeteners among those useful herein include natural and synthetic sweeteners. In one embodiment, the sweetener is a water soluble sweetening agent such as a monosaccharide, a disaccharide or a polysaccharide. For example, water soluble sweetening agents include xylose, ribose, glucose (dextrose), mannose, glatose, fructose (levulose), sucrose (sugar), maltose, a soluble saccharin salt, i.e., a sodium or a calcium saccharin salt, a cyclamate salt, dipeptide based sweeteners, such an L-aspartic acid derived sweetener such as L-aspartyl-L-phenylalaine methyl ester (aspartame). In various embodiments, the sweetener is present at a concentration of from about 0.01% to about 10% by weight of the composition.

In various embodiments, the functional material comprises a therapeutic active. As referred to herein, a therapeutic active is a material that is useful for the prevention or treatment of a physiological disorder or condition. Such disorders or conditions include those of the oral cavity (including the teeth and gingiva). The specific therapeutic active is preferably determined according to the desired utility of the composition. In various embodiments, therapeutic agents useful herein include anticaries agents, tartar control agents, antiplaque agents, periodontal actives, breath freshening agents, malodor control agents, whitening agents, antibacterials, steroids, anti-inflammatory agents, vitamins, proteins, anesthetics, and mixtures thereof.

In certain embodiments, the functional material comprises an oral care active, which is useful for the prevention or treatment of an oral care disorder or condition. Oral care actives among those useful herein include abrasives, anti-caries agents, tartar control agents, antiplaque agents, periodontal actives, breath freshening agents, malodour control agents, tooth desensitizers, salivary stimulants, whitening agents, and combinations thereof. Active materials among those useful herein are described in U.S. Pat. No. 6,596,298, Leung et al. Tartar control agents among those useful herein include dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$; long chain polyphosphates such as sodium hexametaphosphate; and cyclic phosphates such as sodium trimetaphosphate. In some configurations, a polyphosphate is a beta-phase calcium pyrophosphate, such as disclosed in U.S. Pat. No. 6,241,974, White, Jr., incorporated by reference herein Odor reducing agents useful herein include sulfur precipitating agents. Such sulfur-precipitating agents include metal salts, such as a copper salt or a zinc salt. Such salts include copper gluconate, zinc citrate and zinc gluconate.

In certain embodiments, the functional material comprises a saliva stimulating agent (a "succulent"). Such agents include those disclosed in U.S. Pat. No. 4,820,506, Kleinberg et al. In some configurations, a saliva stimulating agent can include a food acid such as citric, lactic, malic, succinic, ascorbic, adipic, fumaric and tartaric acids. In some embodiments, a saliva stimulating agent can be used in the amelioration of dry mouth.

In certain oral care embodiments, the functional material comprises other active materials, such as antibacterial agents such as magnolia extract, triclosan, grapeseed extract, thymol, methyl salicylate, eucalyptol, menthol, hop acids, and cetyl pyridinium chloride; anti-inflammatory agents such a breath freshening agents (for example zinc gluconate, zinc citrate, zinc chlorite and alpha ionone); tooth desensitizers such as potassium nitrate, desensitizing polymers, and desensitizing minerals; anti-inflammatory agents such as magnolia extract, ursolic acid; aloe, and cranberry extract; vitamins such as pantheon, retinyl palmitate, folic acid, tocopherol acetate and Vitamin A; herbs or herbal extracts such as rosemary, oregano, *Chamomilla recutita, Mentha piperita, Salvia officinalis*, orcommiphora and myrrha; proteins, such as milk proteins and enzymes such as peroxide-producing enzymes, amylase, plaque-isrupting agents such as papain, glucoamylase, glucose oxidase, and "next generation" enzymes; whitening agents such as hydrogen peroxide, urea peroxide and phosphate salts; medicinals, such as aspirin (acetyl salicylic acid), caffeine, and benzocaine; probiotics; abrasives such as silicas (including high cleaning silica); anti-caries agents such as stannous salts (e.g., stannous fluoride) or amino fluoride; a nitric oxide synthase inhibitor such as guanidinoethyldisulfide; calcium; anti-attachment ingredients, such as polyumylphosphonic acid; preservatives such as Solbrol® (Bayer Chemicals AG); silicones; chlorophyll compounds, anti-leukoplakia agents such as beta-carotene; anti-oxidants such as Vitamin E; and combinations thereof.

The dispensing system 130 also comprises a conduit 152*a-c* that is operably and fluidly coupled to each of the reservoirs 151*a-c*. Again, in the exemplified embodiment three conduits 152*a-c* are illustrated. However, the invention is not to be so limited and in certain other embodiments the number of conduits 152a-c should be equal to the number of reservoirs and thus the number of conduits can be greater than or less than three. In certain embodiments, the conduits 152a-c comprise or are formed from flexible tubes, such as Teflon® tubing. However, the invention is not to be so limited and the conduits 152a-c may be formed from other tubing, such as PVC piping, metals or other more rigid tubing materials.

Each of the conduits 152a-c is inserted within one of the reservoirs 151a-c so that the oral care additive within the reservoirs 151a-c can be supplied to the oral care implement 110. More specifically, in the exemplified embodiment the conduit 152a is positioned within the reservoir 151a, the conduit 152b is positioned within the reservoir 151b and the conduit 152c is positioned within the reservoir 151c. As will be discussed in more detail below, the conduits 152a-c can supply the oral care additives to the oral care implement 110 (or directly to the test subject's oral cavity when the oral care implement 110 is not used as discussed above) separately, or the conduits 152a-c may converge, via a manifold 156, into a single dispensing conduit 155 that carries the oral care additives, in a mixed form, to the oral care implement 110.

In addition to the conduits 152a-c, the dispensing system 130 also comprises a water conduit 153 that is operably coupled to a water source, which may be a reservoir that is similar to the reservoirs 151a-c but that is filled with water, a faucet, or the like. The water conduit 153 may comprise a flexible tube or a non-flexible tube formed of any of the materials discussed above with regard to the conduits 152a-c. As will be discussed in more detail below, in certain embodiments water is used in creating the oral care formulation so as to provide a constant volume of substances to a test subject's oral cavity when the system 100 is being used to form an oral care formulation. Thus, regardless of whether only one additive is being introduced into the test subject's oral cavity or a plurality of the additives are being introduced into the test subject's oral cavity, the test subject will recognize that the same volume of material is being introduced. This ensures that volume of substances is not a factor during testing that will affect a test subject's feedback regarding the effects experienced during testing, as discussed in more detail below. In other embodiments, water is used as a palate cleanser in between the dispensing of different oral care additives. Thus, a first oral care additive can be dispensed, and then after a certain period of time water can be dispensed to cleanse out the flavor or the like of the first oral care additive, and then a second oral care additive can be dispensed. This can facilitate obtaining the test subject's feedback on multiple different oral care additives in a single testing sequence.

Operably coupled to each one of the conduits 152a-c, 153 is a flow control mechanism 154a-d. In the exemplified embodiment, each of the flow control mechanisms 154a-d is a valve that is alterable between a closed position whereby the additives in the reservoirs 151a-c and the water can not flow through the valves and an open position whereby the additives in the reservoirs 151a-c and the water can flow through the valves. In embodiments that use valves as the flow control mechanisms 154a-d, the reservoirs 151a-c can be pressurized so that upon opening one of the valves 154a-c, the additive within the respective reservoir that is operably coupled to the open valve will begin flowing through its respective conduit to the oral care implement 110. Of course, it should be appreciated that the invention is not limited to using valves as the flow control mechanisms. In other embodiments, the flow control mechanisms 154a-d can be pumps that are fluidly coupled to the reservoirs 151a-c and/or to the conduits 152a-c, 153 so that upon being activated, the pumps will pump the additive from the respective reservoir, into the oral care implement 110 and through the outlet 117. The invention is not to be particularly limited by the structure operating as the flow control mechanism unless specifically recited in the claims.

In the exemplified embodiment, downstream of the flow control mechanisms 154a-d is a manifold 156. In certain embodiments, the manifold 156 is used to mix one or more of the additives together prior to flowing the additives to the oral care implement 110 for dispensing into a test subject's oral cavity. However, as will be discussed in more detail below, in other embodiments the manifold 156 can be omitted and separate conduits can extend from the various reservoirs 151a-c to the oral care implement 110 to separately bring the additives to the oral care implement 110 without mixing thereof or for mixing within the oral care implement 110.

The programmable controller 140 comprises a processor 141, a memory 142 and a timer 143. The processor 141 can be any type of properly programmed processing device, such as a computer or microprocessor. The processor 141 can receive information or data, analyze the received information and data, and transmit instructions to other components in order to ensure that the dispensing system 130 is functioning as intended and operating in accordance with a desired dispensing regimen. The memory 142 of the programmable controller 140 may store algorithms, process recipes and dispensing regimens having dispensing parameters. The dispensing regimens may include instructions regarding which of the oral care additives should be caused to flow from its respective reservoir to the oral care implement at a given time. Thus, the memory 142 and the timer 143 are operably coupled to the processor 141 so that the processor 141 can analyze the process recipes/dispensing regimens that are stored in the memory 142 and provide the necessary instructions to the various components (i.e., flow control mechanisms) for carrying out the process recipes/dispensing regimens.

The display 145 can be any type of device that can display information to a person, such as a scientist who is running an experiment or the like, to determine which oral care formulations are preferred by the test subjects. The input means 150 can be any device, such as a keyboard, a mouse, a touch screen on the display device 145 or the like that enables the person to communicate with the programmable controller 140 to initiate the start of oral care formulation, to make changes to the process recipes/dispensing parameters, to enter test subject feedback or the like. In certain embodiments, the memory 142 of the programmable controller 140 may store a plurality of dispensing regimens. The person running the experiment (or the test subject him or herself) can use the input means 150 to select one of the dispensing regimens. Each of the display 145 and the input means 150 are operably coupled to the programmable controller 140, and more specifically to the processor 141 as illustrated.

The programmable controller 140, and more specifically the processor 141, is operably coupled to each of the flow control mechanisms 154a-d. Through this operable coupling, the programmable controller 140 can control and monitor the operation of the flow control mechanisms 154a-d, whether it be the opening and closing of valves, the activation of a pump, or otherwise, in order to ensure that the additives are supplied to the oral care implement 110 in accordance with a selected dispensing regimen, as discussed in more detail below.

In the exemplified embodiment, each of the conduits 152a-c is positioned within a respective reservoir 151a-c and the water conduit 153 is coupled to a water supply. A different flow control mechanism 154a-d is operably coupled to each of the conduits 152a-c and the water conduit 153 to control flow of the various oral care additives from the reservoirs 151a-c. In the exemplified embodiment, downstream of the flow control mechanisms 154a-d, the conduits 152a-c and the water conduit 153 converge into the manifold 156 and into a single dispensing conduit 155. The dispensing conduit 155 is fluidly coupled to the conduits 152a-c and the water conduit 153 and extends from the conduits 152a-c and the water conduit 153 to the port 116 in the oral care implement 110. Thus, during use, upon a dispensing regimen being selected, one or more of the oral care additives will flow from their respective reservoirs through the conduits to the dispensing conduit 155, to the port 116, through the passageway 118 and through the outlet 117 for dispensing into a test subject's oral cavity. In embodiments that omit the oral care implement, the oral care additives flow from the reservoirs, through the conduits, to the dispensing conduit 155, which dispenses the oral care additives directly into the test subject's oral cavity.

In the exemplified embodiment the dispensing conduit 155 is secured to the handle 111 of the oral care implement 110 by a rubber ring 119. In other embodiments, structures other than the rubber ring 119 can be used to secure the dispensing conduit 155 to the oral care implement 110, such as rope, string, staples, adhesive, tape, glue, fasteners, welding or the like. Securing or coupling the dispensing conduit 155 to the handle 111 may be desirable so that the dispensing conduit 155 does not interfere with the test subject's ability to brush his or her teeth using the oral care implement 110. The invention is not to be so limited and in certain embodiments the dispensing conduit 155 may not be secured to the oral care implement 110 at all. Furthermore, the combined length of the conduits 152a-c, 153 and the dispensing conduit 155 is sufficient to enable a test subject to manipulate the oral care implement 110 for toothbrushing despite the oral care implement 110 being fluidly coupled to the dispensing system.

Figure 2:
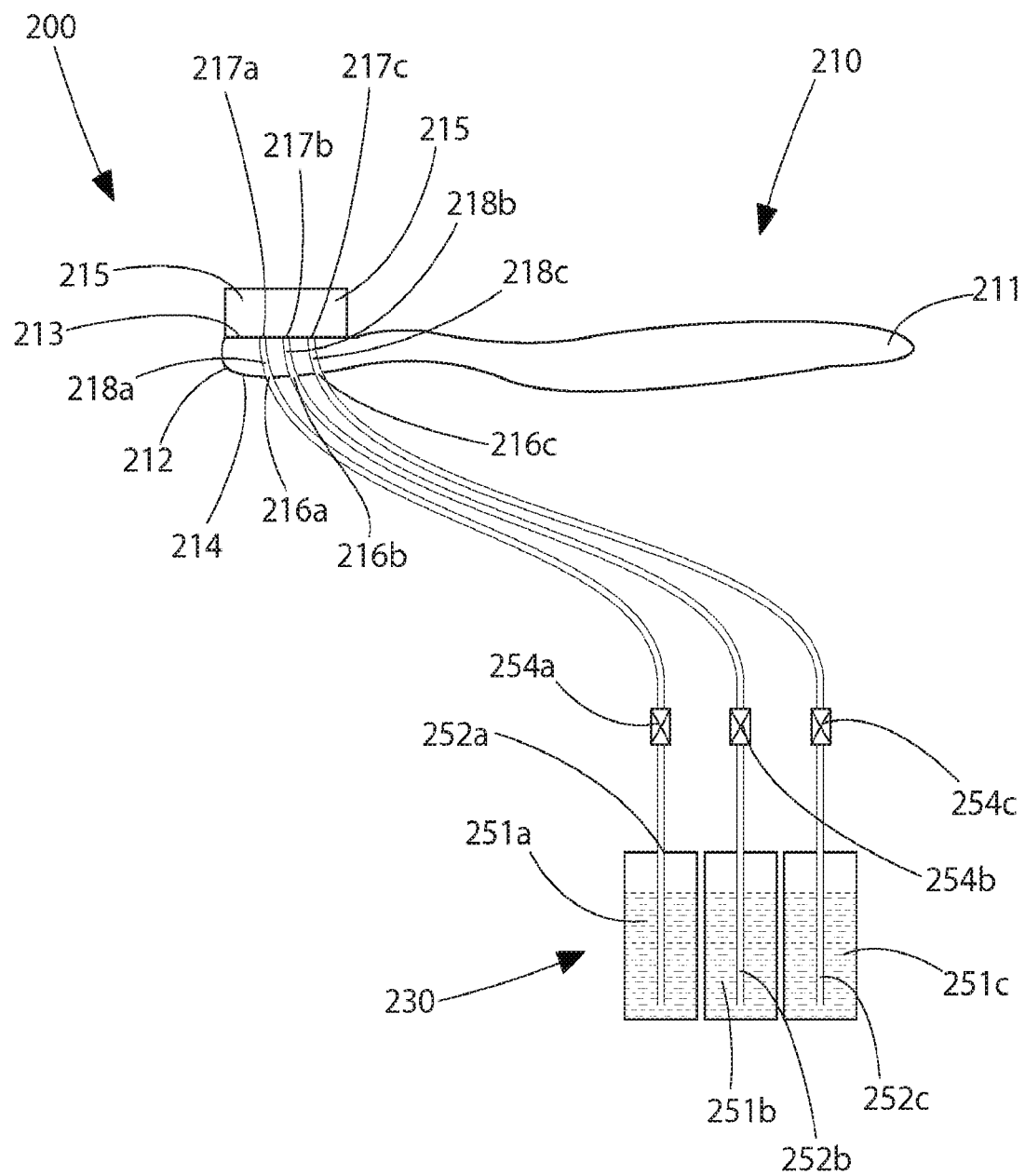
FIG. 2 is a schematic illustration of a system for making an oral care formulation in accordance with another embodiment of the present invention.

Although the invention is illustrated whereby the conduits 152a-c and 153 converge into the dispensing conduit 155 prior to the additives flowing into the oral care implement 110, the invention is not to be limited by this particular arrangement. Referring to FIG. 2, a system 200 for creating an oral care formulation will be described in accordance with a second embodiment of the present invention. Certain components of the system 200 will not be described in detail, it being understood that they are the same as the components of the system 100. Components of the system 200 that are similar to components of the system 100 will be similarly numbered, except the 200-series of numbers will be used. Furthermore, in FIG. 2 the programmable controller 140, the display 145 and the input means 150 are not illustrated. However, these components are operably coupled to each other and to the flow control mechanisms in the same manner as depicted in FIG. 1.

In the embodiment of FIG. 2, the system 200 comprises an oral care implement 210 having a handle 211 and a head 212. The head comprises a first port 216a, a second port 216b and a third port 216c, each of which forms an opening into a rear surface 214 of the head 212. The first port 216a is fluidly coupled to a first outlet 217a via a first passageway 218a, the second port 216a is fluidly coupled to a second outlet 217b via a second passageway 218b, and the third port 216c is fluidly coupled to a third outlet 217c via a third passageway 218c. Each of the first, second and third outlets 217a-c form an opening on the front surface 213 of the head 212 for dispensing additives to the test subject's oral cavity. Each of the first, second and third outlets 217a-c form openings that are isolated and spaced apart from one another along the front surface 213 of the head 212. In the exemplified embodiment the outlets 217a-c are spaced apart along the longitudinal axis of the head 212. However, the invention is not to be so limited and the outlets 217a-c can be spaced apart along a transverse axis or the like. Furthermore, although described herein with the ports 216a-c formed into the head 112 of the oral care implement 110, the invention is not to be so limited. In certain embodiments the ports 216a-c can be formed into other parts of the oral care implement 110, such as in the handle 111 of the oral care implement 110, and passageways can be formed into the oral care implement 110 that lead from the ports 216a-c to the outlets 217a-c.

The system 200 further comprises a dispensing system 230 comprising a programmable controller (not illustrated), a display (not illustrated), an input means (not illustrated), a first reservoir 251a, a second reservoir 251b, a third reservoir 251c, a first conduit 252a, a second conduit 252b and a third conduit 252c, a first flow control mechanism 254a, a second flow control mechanism 254b and a third flow control mechanism 254c (the details of the components indicated as not illustrated can be found with reference to FIG. 1 and the relevant description). The first conduit 252a extends from the first reservoir 251a to the first port 216a, the second conduit 252b extends form the second reservoir 251b to the second port 216b and the third conduit 252c extends from the third reservoir 251c to the third port 216c. Each of the first, second and third reservoirs 251a-c contains an oral care additive. In certain embodiments, one of the additives can be water. The materials, specific features and structures of the various components of the system 200 are the same as the similar features of the system 100 and therefore will not be repeated herein for brevity.

In the system 200, the various conduits 252a-c do not converge into a single conduit prior to reaching the oral care implement 210. Rather, each of the conduits 252a-c separately extends to the oral care implement 210 for separately dispensing an oral care additive to the oral care implement. More specifically, the first oral care additive in the first reservoir 251a will flow through the first conduit 252a to the first port 216a, through the first passageway 218a and out to the oral cavity of the test subject through the first outlet 217a. The second oral care additive in the second reservoir 251b will flow through the second conduit 252b to the second port 216b, through the second passageway 218b and out to the oral cavity of the test subject through the second outlet 217b. The third oral care additive in the third reservoir 251c will flow through the third conduit 252c to the third port 216c, through the third passageway 218c and out to the oral cavity of the test subject through the third outlet 217c. Thus, using the system 200, the various oral care additives will not be mixed until they are within the oral cavity of the test subject. This can be beneficial for certain oral care additives that have an effective use within a short time frame after being mixed with other oral care additives.

Figure 3:
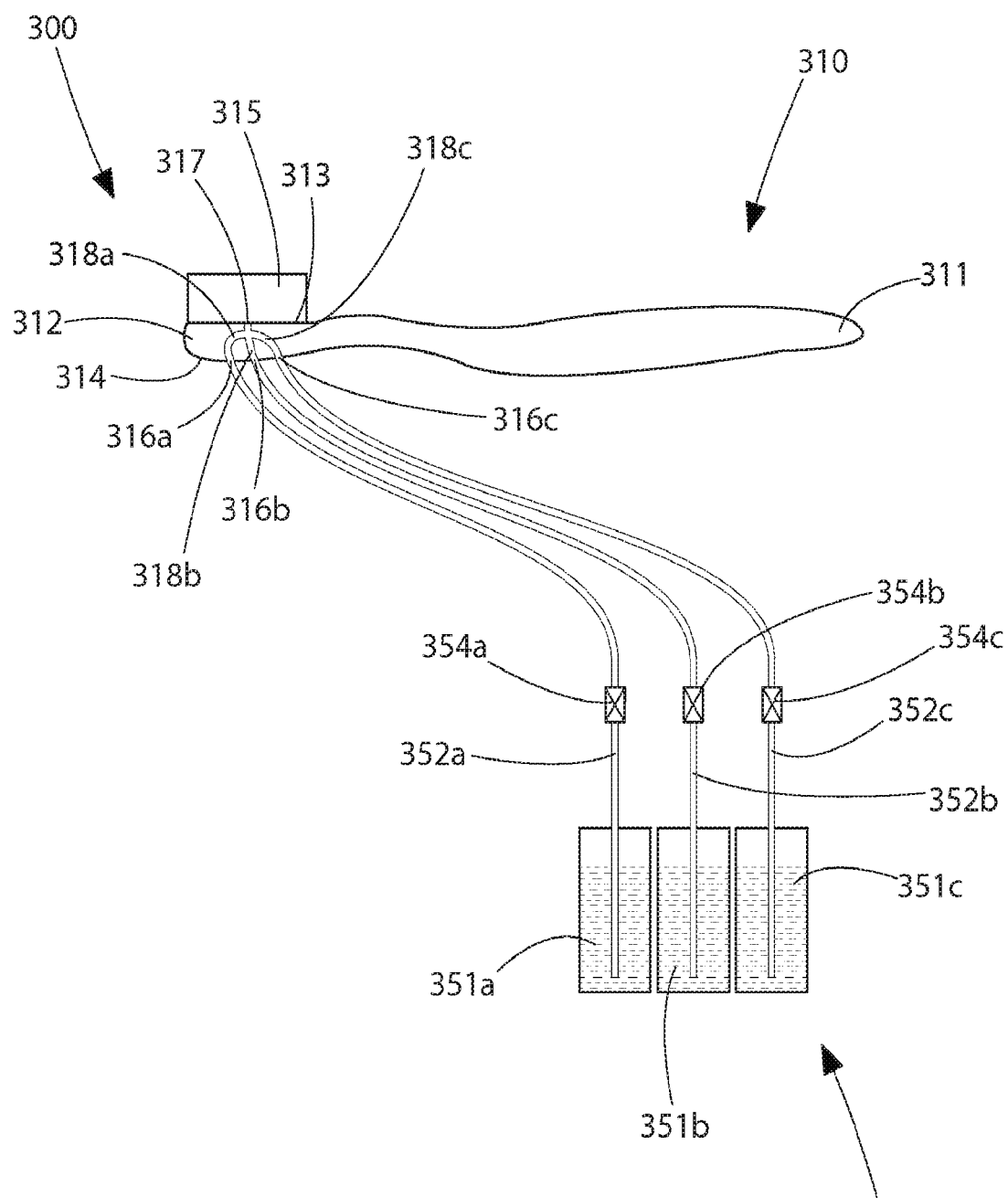
FIG. 3 is a schematic illustration of a system for making an oral care formulation in accordance with yet another embodiment of the present invention.

Referring now to FIG. 3, a system 300 for making an oral care formulation in accordance with yet another embodiment will be described. The system 300 is similar to the system 200 and features of the system 300 that are the same as features of the system 200 will be similarly numbered except that the 300-series of numbers will be used. Furthermore, features of the system 300 that are similar to features of the system 200 will not be described in detail, it being understood that the description of the similar feature with regard to the system 200 applies.

In FIG. 3, the system 300 is the same as the system 200 of FIG. 2 except that there is only one outlet 317 forming an opening in the front surface 313 of the head 312. Thus, as the oral care additives flow into the first, second and third ports 316a-c and through the first, second and third passageways 318a-c, the additives then mix and combine within the oral care implement 310, and more specifically within the head 312 of the oral care implement 310. Specifically, the first, second and third passageways 318a-c converge at a dispensing passageway which extends from the passageways 318a-c to the outlet 317. As a result, if one or more oral care additives are dispensed simultaneously in accordance with the dispensing regimen, the one or more oral care additives will mix within the oral care implement 310, and specifically within the head 312 of the oral care implement 110, prior to being dispensed to the oral cavity of the test subject through the outlet 317.

As is evident from the depiction of the system 100 in FIG. 1, the dispensing system 130, including the reservoirs 151a-c, is external to the oral care implement 110. Thus, the dispensing system 130, in at least some embodiments, is not provided within the handle 110 of the oral care implement 110 or otherwise. Rather, the dispensing system 130 is separate from the oral care implement 110 and merely fluidly coupled to the oral care implement 110 via the conduit 155. This is true for each of the systems 100, 200, 300. The oral care implement 110, 210, 310 is operably and fluidly coupled to the dispensing system 130, 230, 330 via fluid coupling of the dispensing conduit 155 to the oral care implement 110 (in FIG. 1) or via direct attachment of the conduits 252a-c, 352a-c to the oral care implement 210, 310 (in FIGS. 2 and 3).

Referring again to FIG. 1, a method of making an oral care formulation utilizing the system 100 depicted in FIG. 1 will be described. Although the method is being described below with reference to FIG. 1, it should be appreciated that the system 200 of FIG. 2 or the system 300 of FIG. 3 can utilize the same method for making an oral care formulation, the difference being whether the oral care additives mix before reaching the oral care implement (FIG. 1), within the oral care implement (FIG. 3) or not at all (FIG. 2). In certain aspects, the method is used in a testing situation when it is desired to obtain a test subject's feedback regarding one or more oral care formulations. The test subject can brush his or her teeth using the oral care implement 110 on one or more occasions under testing conditions while different oral care formulations are created in-situ in the manner described below. Alternatively, the test subject can rinse his or her mouth while different oral care formulations are created in-situ in the manner described below when the oral care implement 110 is not used and the oral care additives are instead directly injected/dispensed into the test subject's oral cavity. The test subject can then, both during and after brushing/rinsing, provide feedback regarding the oral care formulations so that an oral care formulation that is most favored by the testing subjects can be manufactured and commercialized.

In the method, a first dose of an oral care formulation base is applied to the oral cavity of the test subject. In certain embodiments the first dose of the oral care formulation base may include a maximum of 1.5 grams, or between 1.0 to 1.5 grams, or between 0.5 to 1.5 grams of a toothpaste product. The oral care formulation base can alternatively be an amount of a rinsing formula, or any other type of base product for oral care that can be modified by the oral care additives. In certain embodiments, the oral care formulation base is a flavorless oral care formulation that can be modified by mixing additives with the oral care formulation base in order to provide a user with a sensation such as flavor, tingle, cool, hot, medicinal or the like. In certain embodiments, in its base form, before additives are added thereto, the oral care formulation base is flavorless and devoid of oral care additives and therefore provides no sensations to a user or test subject. However, as discussed above the invention is not to be so limited in all embodiments and in other embodiments the oral care formulation base may include some flavors or the like even before the oral care additives are dispensed.

In one embodiment, the first dose of the oral care formulation base can be applied to the oral cavity of the test subject by dispensing the first dose of the oral care formulation base onto the oral care implement 110 (such as on the tooth cleaning elements 115 or otherwise on the head 112 of the oral care implement 110) and then having the test subject brush his or her teeth with the oral care implement 110 or otherwise contacting the test subject's oral cavity with the oral care implement loaded with the first dose of the oral care formulation base. Of course, the invention is not to be so limited in all embodiments and the oral care formulation base can be applied to the oral cavity of the test subject in other manners as desired (i.e., pouring a rinse formula into a test subject's oral cavity, applying the oral care formulation base with the test subject's finger, etc.). Furthermore, in other embodiments the method may not include an oral care formulation base at all. Rather, in such embodiments the invention is directed to the system described herein above and to a method of dispensing oral care additives into the oral cavity of a test subject in accordance with a dispensing regimen without first providing an oral care formulation base to the oral cavity of the test subject.

In certain embodiments, before the test subject begins applying the oral care formulation base to his or her oral cavity, a user (which can be a scientist or experiment leader, the test subject or any other third person) will select a first dispensing regimen. The selection of the first dispensing regimen can be accomplished by the user communicating with the program controller 140 via the input means 150 and the display 145. In one embodiment, the user can scroll through a list of a plurality of pre-programmed dispensing regimens (which may be displayed on the display 145) to then select a desired dispensing regimen. Alternatively, the user can select various oral care additives to be dispensed at various times and thereby create the dispensing regimen, which can then be saved in the memory 142 of the programmable controller 140. Still further, the user may select one of the pre-stored dispensing regimens and use the input means 150 to make modifications to the pre-stored dispensing regimen by changing the dispensing period of the oral care additives, the number of oral care additives dispensed, the identity of the oral care additives dispensed, the sequence of the oral care additives dispensed or the like to create the first dispensing regimen.

After the first dispensing regimen has been selected, the programmable controller 140 will begin executing the selected first dispensing regimen to dispense one or more of the oral care additives from the reservoirs 151a-c and from the water source into the oral cavity via the oral care implement 110 or otherwise. The dispensing of one or more of the oral care additives will be accomplished in accordance with dispensing parameters of the selected first dispensing regimen. The parameters of the dispensing regimens include, without limitation, amount or concentration of oral care additives, temporal dispensing period of oral care additives, number of oral care additives dispensed, identity of oral care additives dispensed, sequence of oral care additives dispensed and time delay before dispensing oral care additives. Thus, depending on which dispensing regimen is selected, the above parameters are modified and changed in order to test out various different combinations of oral care additives in various differing amounts and at various dispensing time intervals. In certain embodiments, the same or different oral care additives can be dispensed in pulses at different time points during a single testing/brushing session (e.g., oral care additive one dispensed from time zero to time ten, oral care additive two dispensed from time fifteen to time twenty-five, oral care additive one dispensed from time thirty to time forty, etc.).

The dispensing regimen will determine at what time intervals one or more of the oral care additives are dispensed into the oral cavity of the test subject, the concentration levels of the one or more additives that are dispensed into the oral cavity, the length of time during which the one or more additives are dispensed into the oral cavity, the sequence at which the one or more additives are dispensed into the oral cavity and the like. In certain embodiments, the dispensing regimen may include waiting a time period after the test subject begins brushing and then dispensing one additive into the oral cavity. In another embodiment, the dispensing regimen may include waiting a time period after the test subject begins brushing and then dispensing two or more additives into the oral cavity simultaneously. In yet another embodiment, the dispensing regimen may include waiting a time period after the test subject begins brushing, then dispensing a first additive into the oral cavity for a time period, and then adding one or more additional additives into the oral cavity while still adding the first additive or after stopping adding the first additive. Any different dispensing regimen can be used, any number of different oral care additives can be dispensed simultaneously or at different times, and a virtually unlimited number of different oral care formulations can be created in-situ in the testing subject's oral cavity using the inventive system and method.

According to the instructions or dispensing parameters of the selected first dispensing regimen, one or more of the oral care additives, at the same or different temporal times and for the same or different dispensing periods, are dispensed from their respective reservoirs to the outlet 117 in the oral care implement 110 for dispensing. The programmable controller 140 actuates one or more of the flow control mechanisms 154a-d (by opening valves, actuating pumps or the like) in a sequence so that one or more of the oral care additives are dispensed to the oral cavity of the test subject in accordance with the dispensing parameters of the selected first dispensing regimen. In certain embodiments, when the oral care additives are dispensed, the test subject is already contacting his or her oral cavity with the oral care implement having the oral care formulation base thereon. In certain other embodiments, when the oral care additives are dispensed, the test subject is rinsing his or her oral cavity with a rinse formula as the oral care formulation base. Thus, when the oral care additives are dispensed through the outlet 117 into the test subject's oral cavity, the oral care additives mix with the oral care formulation base. This mixing of the oral care additives with the oral care formulation base creates, in the test subject's oral cavity, an oral care formulation such as a toothpaste that could be purchased by a consumer at a retail store having various flavors and other benefits. Thus, the oral care additives mix with the oral care formulation base in-situ within the oral cavity of the test subject to form an oral care formulation.

As the oral care additives are mixed with the oral care formulation base, the test subject continues brushing his or her teeth by continuing to contact the oral care implement 110 with his or her oral cavity or rinsing his or her mouth without the oral care implement 110 as discussed above. The test subject will, at this time, be brushing or contacting his or her teeth with a potential oral care formulation that may possibly be created for consumer use depending on the feedback that is provided by the test subject. Thus, either while the test subject is contacting his or her oral cavity with the oral care formulation (the oral care formulation mixed with the oral care additives in-situ) or after the test subject has completed contacting his or her oral cavity with the oral care formulation, the test subject will provide feedback regarding effects experienced by the test subject during the brushing. This feedback may include the test subject indicating, on a scale, in response to survey questions or the like, whether the experience was "not fresh at all" or "the freshest sensation possible" or some sensation in between. The feedback may also include the test subject indicating, on a scale, in response to survey questions or the like, whether the experience was "not clean" or "very clean" or some cleanliness in between. The feedback can be categorized as positive feedback or negative feedback and may be categorized on a scale or not.

In certain embodiments, the feedback may be provided by the test subject using the input means 150 and transmitting the feedback to the processor 141 of the programmable controller 140. In other embodiments, the feedback may be provided by the test subject filling out a survey either on a computer or by pen and paper. In certain other embodiments, the feedback may be provided by the test subject answering questions or otherwise providing feedback on a computer that is separate from the programmable controller 140. The feedback can be the test subject providing answers on a scale of one to ten regarding a variety of questions, such as how fresh was the brushing experience, how clean does your mouth feel, did you enjoy the brushing experience, did you enjoy the flavor of the oral care formulation, did you enjoy the sensations provided by the oral care formulation, was the timing of the flavor/sensation bursts favorable and/or enjoyable, and the like. In certain embodiments, the test subject will provide the feedback before toothbrushing, during toothbrushing, and one or more times after toothbrushing. In one embodiment, the one or more times after toothbrushing may include the test subject providing feedback seven times after toothbrushing at ten minute intervals to provide an indication regarding how long and to what degree the clean feeling or fresh feeling remained with the test subject after application thereof to the test subject's oral cavity.

After the feedback is provided, a determination can be made whether to create an oral care formulation for consumer use using the first dispensing regimen. This determination is dependent upon the feedback that is provided by the test subject. Thus, in certain embodiments if the test subject, or multiple test subjects, provide negative feedback regarding an oral care formulation that was created using a particular dispensing regimen, that oral care formulation will not be created for consumer use. However, if the test subject, or multiple test subjects, provides positive feedback regarding an oral care formulation that was created using a particular dispensing regimen, that oral care formulation will be created for consumer use. The testing that takes place using the inventive system and method is designed to find the optimal ingredient (i.e., oral care additive) levels, ingredient delivery timing and the like to achieve a maximum perception of freshness and cleaning to a consumer and test subject. In certain embodiments, if an oral care formulation is created for consumer use in accordance with a dispensing regimen based on feedback provided by the test subject, the oral care formulation will further be packaged for consumer use and the packaged oral care formulation for consumer use will be distributed to consumers, such as by being displayed for sale on shelves at retail stores.

When it is desired to create an oral care formulation for consumer use, that oral care formulation will have the same recipe in the same concentrations and with the same time intervals for flavor and sensation bursts for providing the same sensations and effects as did the mixture of the dose of the oral care formulation base and the one or more additives that were created in-situ within the oral cavity of the test subject. Thus, for example, in one embodiment if positive feedback was provided based on an in-situ created oral care formulation formed by an oral care additive that was added at some time interval (i.e. twenty seconds) into the test subject's brushing, the oral care formulation for consumer use will mimic the in-situ created oral care formulation. Specifically, such an oral care formulation for consumer use may include capsules that release the oral care additive at the same time interval (i.e., twenty seconds) into a normal consumer's toothbrushing session. Such capsules would be designed to dissolve or abrade in coordination or reflection of that first time interval (i.e., twenty seconds). Alternatively, such an oral care formulation for consumer use may include flakes that release the oral care additive at the same time interval (i.e., twenty seconds) into a normal consumer's brushing session. In another embodiment, if positive feedback was received based on a dispensing regimen that dispensed a first oral care additive from time zero to time ten seconds and released a second oral care additive from time twenty seconds to time thirty seconds, then the oral care formulation created for consumer use would mimic that dispensing pattern, concentration and/or timing of oral care additive delivery into the oral cavity. Various combinations of capsules, flakes or other techniques for dispensing oral care additives at various times during a toothbrushing session can be used. Thus, any technique for creating an oral care formulation for consumer use that mimics the effects that were achieved by the relevant dispensing regimen can be used.

In certain embodiments, it may be desirable to compare test subject feedback on two or more different oral care formulations that are created in-situ using two or more different dispensing regimens in order to determine which of the oral care formulations should be created for consumer use. In certain embodiments, one or more additives may be dispensed to the oral cavity in accordance with a first dispensing regimen while a first dose of an oral care formulation base is being applied to an oral cavity of a test subject. The test subject will then provide feedback regarding effects experienced while the test subject was brushing his or her teeth with the oral care additives being dispensed in accordance with the first dispensing regimen. After receiving the test subject's feedback, the method may then include modifying the first dispensing regimen based on the feedback to create a second dispensing regimen, the second dispensing regimen being different than the first dispensing regimen in at least one dispensing parameter (i.e., concentration of oral care additives, timing if oral care additive dispensing, temporal dispensing period of oral care additives, number and/or sequence of oral care additives dispensed, identity of oral care additives dispensed, etc.). Specifically, the second dispensing regimen may be different than the first dispensing regimen by changing one or more of the sequence that the oral care additives were dispensed, changing the length of time that the oral care additives were dispensed, changing the number and identity of the oral care additives that were dispensed, or the like.

Next, in accordance with the inventive method, a second dose of the oral care formulation base can be applied to the oral cavity of the test subject. This may involve the second dose of the oral care formulation base being dispensed onto the tooth cleaning elements 115 of the oral care implement 110, and then the test subject brushing his or her teeth using the oral care implement 110. Of course, other techniques for applying the second dose of the oral care implement base onto the oral cavity of the test subject can be used as has been described in detail above. While the second dose of the oral care formulation base is being applied to the oral cavity of the test subject, the method includes dispensing one or more additives to the oral cavity in accordance with the second dispensing regimen. The one or more oral care additives of the second dispensing regimen mix with the second dose of the oral care formulation base in-situ within the oral cavity of the test subject.

After the test subject finishes applying the oral care formulation base mixed with the oral care additives of the second dispensing regimen to the test subject's oral cavity (such as by toothbrushing), the test subject provides feedback regarding effects experienced by the test subject during such application of the oral care formulation base mixed with the oral care additives of the second oral care regimen. The feedback can be provided in any of the manners noted above and can involve a specific comparison of the first and second dispensing regimens.

Finally, after the feedback is obtained, the method includes creating an oral care formulation for consumer use based on the feedback. In certain embodiments, the creation of the oral care formulation for consumer use can be based on the feedback obtained regarding the effects experienced by the test subject while the oral care additives were being dispensed in accordance with the first dispensing regimen and the feedback obtained regarding the effects experienced by the test subject while the oral care additives were being dispensed in accordance with the second dispensing regimen. Specifically, in accordance with certain embodiments of the invention, the feedback obtained regarding the effects experienced by the test subject while the oral care additives were being dispensed in accordance with the first dispensing regimen is compared with the feedback obtained regarding the effects experienced by the test subject while the oral care additives were being dispensed in accordance with the second dispensing regimen. The comparison of the various feedbacks can be used to determine whether the first dispensing regimen or the second dispensing regimen was more favored by the test subject based on analyzing which had more positive or better feedback. In such embodiments, the creation of the oral care formulation for consumer use may comprise creating the oral care formulation from the one of the first and second dispensing regimens that received more positive or better feedback. The more positive/better feedback determination can be made based on a review of scores provided by the test subject, answers to subjective questions provided by the test subject, answers to yes or no questions provided by the test subject, comparisons of the dispensing regimens provided by the test subject, or ratings of cleanliness, freshness, enjoyability and the like provided by the test subject.

Furthermore, although the above has been described where only a first and a second dispensing regimen are used, the invention is not to be so limited. In certain embodiments, the process of having a test subject apply an oral care formulation base to his or her oral cavity, dispensing oral care additives based on a dispensing regimen and obtaining feedback from the test subject can occur as many times as desired. Thus, a test subject can test three, four, five, ten or more dispensing regimens and provide feedback on each of the testing regimens. Then, the oral care formulation that is created for consumer use can be the one that received the best feedback from the test subject. Furthermore, in certain embodiments feedback from multiple test subjects can be used and the more positive feedback or the best feedback referred to herein can be based on a collective analysis of the feedback from all of the test subjects.

Figure 4:
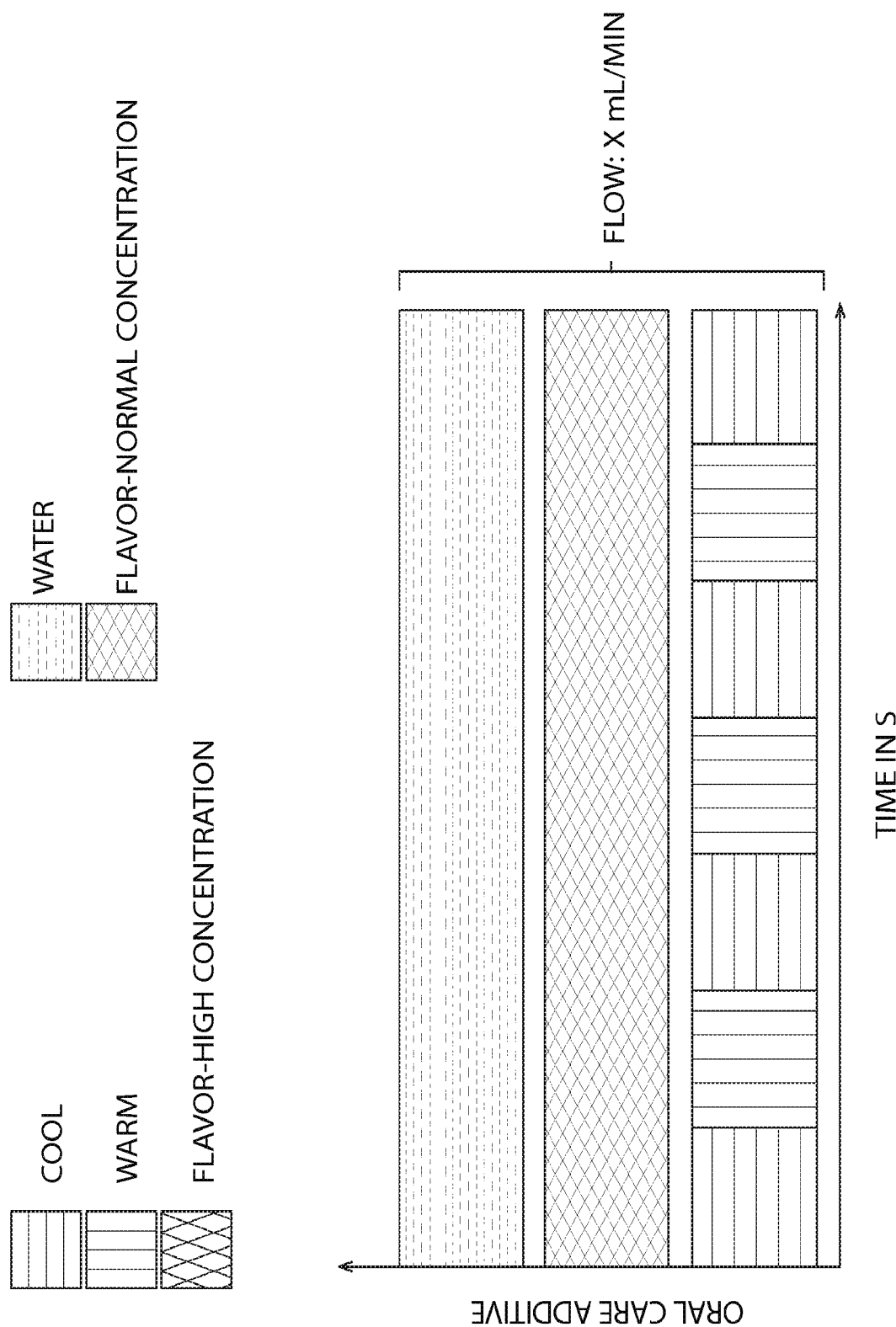
FIG. 4 is a graphical representation of a dispensing regimen in accordance with a first embodiment of the present invention.

Referring now to FIG. 4, one embodiment of a dispensing regimen will be described. FIG. 4 provides a graphical representation of a dispensing regimen. In the dispensing regimen of FIG. 4, the oral care additives that are being dispensed are indicated as being "cool" and "warm." Thus, the oral care additives can be any oral care additive that provides a "cool" sensation to a test subject (e.g., menthol, camphor, maltitol syrup, sorbitol, mannitol, erythritol, isomalt, xylitol or the like) and any oral care additive that provides a "warm" sensation to a test subject (e.g., capsaicin or the like). The graph has the oral care additive on the y-axis and the time in seconds on the x-axis.

In accordance with the dispensing regimen depicted in FIG. 4, water is dispensed continuously throughout the toothbrushing or throughout the time that the programmable controller is executing the dispensing regimen. Furthermore, the cool and warm additives are dispensed in alternative fashion throughout the dispensing regimen. Specifically, first the cool additive is dispensed, followed by the warm additive, followed by the cool additive, the warm additive, the cool additive, followed by the warm additive, and finally followed again by the cool additive. Furthermore, in this embodiment the cool and warm additives are dispensed at a flavor-normal concentration.

Figure 5:
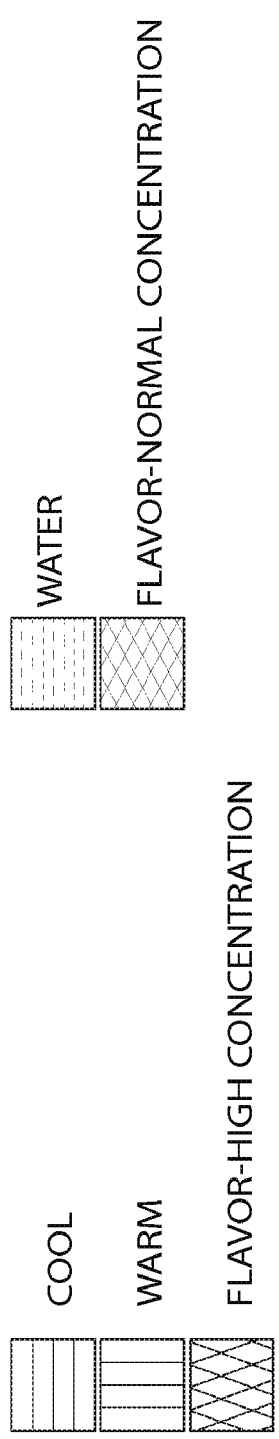
FIG. 5 is a graphical representation of a dispensing regimen in accordance with a second embodiment of the present invention.
Figure 5:
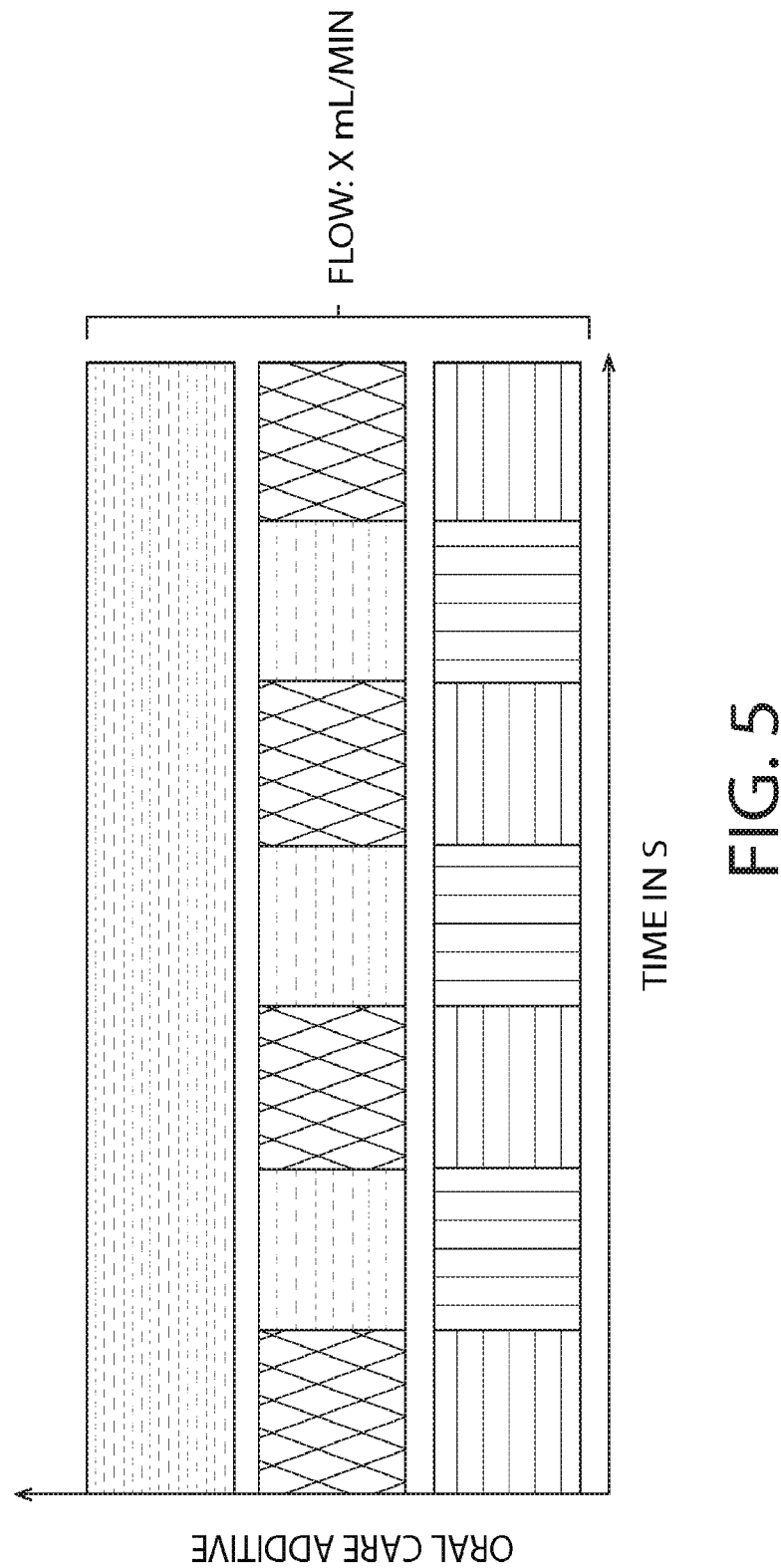

Referring now to FIG. 5, another dispensing regimen will be described. The dispensing regimen of FIG. 5 is similar to the dispensing regimen of FIG. 4 in that water is dispensed throughout the dispensing regimen and the cool and warm additives are alternatingly dispensed. However, the dispensing regimen of FIG. 5 differs from the dispensing regimen of FIG. 4 in that the cool additive is always dispensed at a high flavor concentration and the warm additive is always dispensed simultaneously with an additional water dispensing. Thus, if the dispensing regimen of FIG. 4 was first used and the feedback obtained from the test subject is that the cool additive was not noticeable, the next dispensing regimen might be the dispensing regimen of FIG. 5 to provide a higher concentration of the cool additive.

Figure 6:
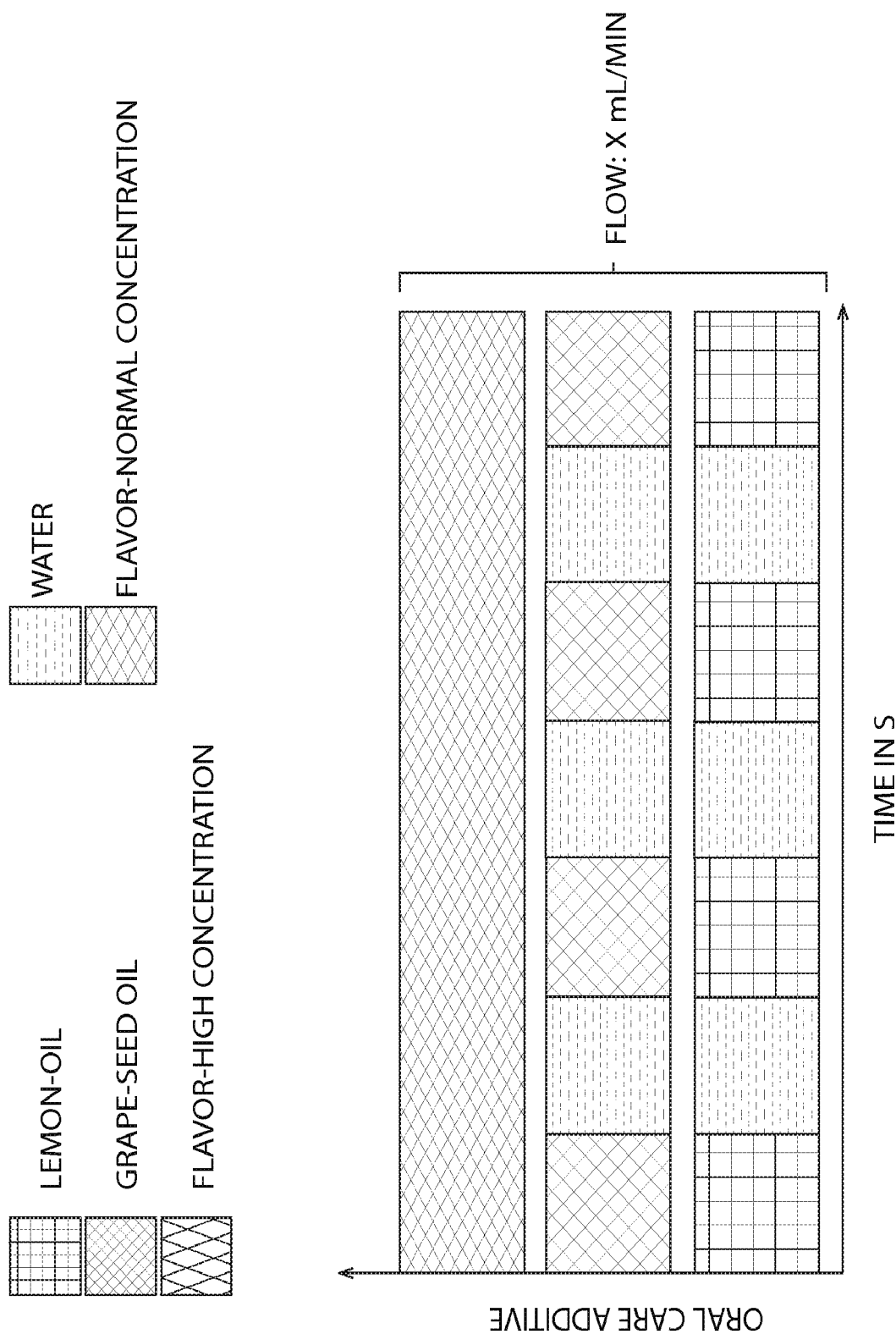
FIG. 6 is a graphical representation of a dispensing regimen in accordance with a third embodiment of the present invention.

Referring to FIG. 6, yet another dispensing regimen will be described. In FIG. 6, the additives include lemon-oil, grape-seed oil and water, and they can again be dispensed at high or normal concentrations. In the embodiment of FIG. 6, the dispensing regimen is consistently dispensing the additives at the normal concentration. Furthermore, the dispensing regimen alternatingly dispenses the grape-seed oil and water while also alternatingly dispensing the lemon-oil and water.

Figure 7:
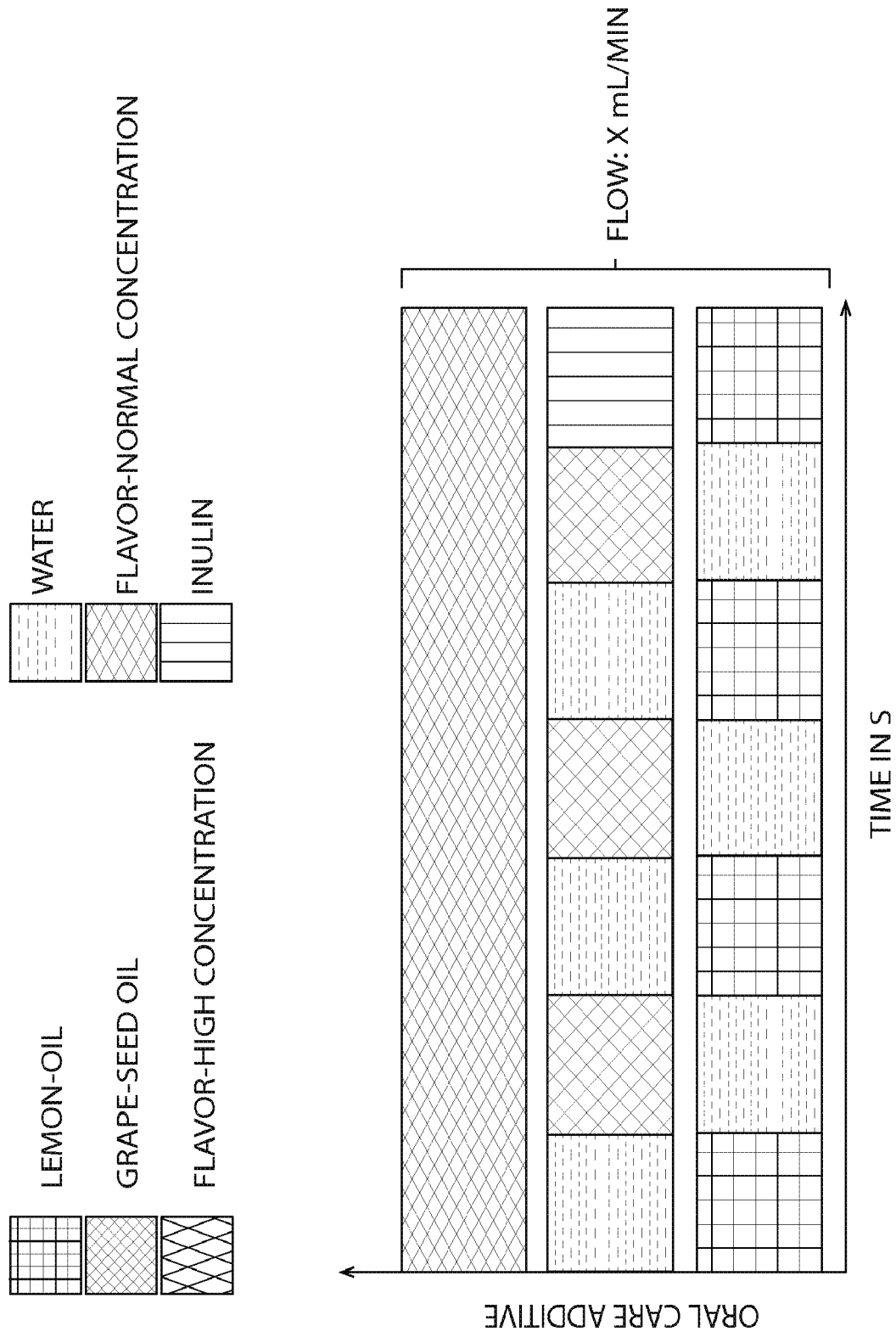
FIG. 7 is a graphical representation of a dispensing regimen in accordance with a fourth embodiment of the present invention.

Referring to FIG. 7, a final dispensing regimen will be described. In FIG. 7, the additives again include lemon-oil, grape-seed oil and water, and also include inulin. In this embodiment, the additives are again dispensed at the flavor normal concentration throughout the dispensing regimen. However, in this embodiment the water and the grape-seed oil are alternatingly dispensed and the lemon-oil and water are alternatingly dispensed so that the water is being dispensed out of phase. Thus, the water in the water/lemon-oil dispensing is never dispensed at the same time as the water in the water/grape-seed oil dispensing. Furthermore, in this embodiment the last item dispensed in the water/grape-seed oil dispensing line is inulin. It should be appreciated and understood that the dispensing regimens graphically depicted in FIGS. 4-7 are for exemplary purposes only and are not limiting of the present invention. Many additional oral care additives can be used in the dispensing regimens in addition to those illustrated in FIGS. 4-7, and the intervals, sequences, number of oral care additives dispensed, and temporal dispensing periods of the various oral care additives can be different than that illustrated As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A method of making an oral care formulation for consumer use, the method comprising:
   a) providing to a test subject an oral care formulation base and one or more oral care additives;
   b) obtaining feedback from the test subject regarding effects experienced by the test subject during the performance of step a); and
   c) creating the oral care formulation for consumer use based, at least in part, on the feedback; wherein:
   step a) comprises:
      i) providing a first dose of an oral care formulation base to an oral cavity of a test subject; and
      ii) dispensing one or more oral care additives to the oral cavity in accordance with a first dispensing regimen during the performance of step i), the one or more oral care additives mixing with the first dose of the oral care formulation base in-situ within the oral cavity of the test subject;
      wherein the dispensing regimen of step ii) contains instructions, or dispensing parameters, such that the selected oral care additives are dispensed at the same or different temporal times and for the same or different dispensing periods; and
   wherein steps (a)-(c) are performed using a system comprising:
   an oral care implement comprising one or more outlets; and
   a dispensing system comprising:
      one or more reservoirs of oral care additives;
      one or more conduits fluidly coupling the one or more reservoirs to the one or more outlets of the oral care implement;

a programmable controller; and one or more flow control mechanisms operably coupled to the one or more reservoirs, the programmable controller operably coupled to the one or more flow control mechanisms to actuate the one or more flow control mechanisms in a manner such that the one or more oral care additives are dispensed via the outlets of the oral care implement in accordance with dispensing parameters of a selected dispensing regimen;

wherein the dispensing system is external to the oral care implement.

2. The method according to claim 1 further comprising:

d) wherein the oral care formulation based on the feedback obtained in step b) is packaged for consumer use; and e) distributing the packaged oral care formulation for consumer use to consumers.

3. The method according to claim 1 wherein the oral care formulation for consumer use created in step c) comprises the oral care formulation base and at least one of the one or more oral care additives.

4. The method according to claim 1 wherein step a) further comprises:

a-1) contacting one or more oral surfaces of the oral cavity with an oral care implement loaded with the first dose of the oral care formulation base.

5. The method according to claim 4 wherein the oral care implement comprises one or more ports and one or more outlets in fluid communication with the one or more ports, the one or more ports fluidly coupled to one or more reservoirs containing the one or more oral care additives, and wherein step b) further comprises:

b-1) flowing the one or more oral care additives from the one or more reservoirs to the one or more ports in accordance with the first dispensing regimen; and b-2) the one or more oral care additives dispensing from the one or more outlets of the oral care implement to mix with the first dose of the oral care formulation base during performance of step a-1).

6. The method according to claim 5 wherein the oral care implement is a toothbrush and the one or more outlets are located in a head of the toothbrush.

7. The method according to claim 6 wherein the one or more outlets are located in a front surface of the head of the toothbrush, and the toothbrush further comprises a plurality of tooth cleaning elements extending form the front surface of the head.

8. The method according to claim 5 wherein the one or more reservoirs are part of the dispensing system, the dispensing system further comprising the programmable controller, the one or more conduits fluidly coupling the one or more reservoirs to the oral care implement, and the one or more flow control mechanisms operably coupled to the one or more reservoirs, the programmable controller operably coupled to the one or more flow control mechanisms to actuate the one or more flow control mechanisms in a manner such that the one or more oral care additives are dispensed to the oral cavity in accordance with dispensing parameters of the first dispensing regimen.

9. The method according to claim 1 wherein step c) further comprises:

c-1) modifying the first dispensing regimen based on the feedback of step b) to create a second dispensing regimen, the second dispensing regimen being different than the first dispensing regimen in at least one dispensing parameter;

c-2) providing a second dose of the oral care formulation base to the oral cavity of the test subject;

c-3) dispensing one or more oral care additives to the oral cavity in accordance with the second dispensing regimen during the performance of step c-2), the one or more oral care additives of the second dispensing regimen mixing with the second dose of the oral care formulation base in-situ within the oral cavity of the test subject;

c-4) obtaining feedback regarding effects experienced by the test subject during the performance of step c-3); and c-5) creating the oral care formulation for consumer use based, at least in part, on the feedback of step c-4).

10. The method according to claim 9 further comprising comparing the feedback obtained in step b) with the feedback obtained in step c-4) to determine whether the first dispensing regimen or the second dispensing regimen received better feedback, and wherein step c-5) comprises creating the oral care formulation for consumer use from one of the first and second dispensing regimens that received the better feedback.

11. The method according to claim 9 wherein steps c-2) through c-4) are repeated for three or more different dispensing regimens and wherein step d-5) comprises creating the oral care formulation for consumer use from one of the dispensing regimens that received better feedback.

12. The method according to claim 9 wherein the at least one parameter is selected from a group consisting of amount of oral care additives, temporal dispensing period of oral care additives, number of oral care additives dispensed, identity of oral care additives dispensed, and sequence of oral care additives dispensed.

13. The system according to claim 1 wherein the one or more conduits comprise flexible tubes.

* * * * *